United States Patent
Katouzian et al.

(10) Patent No.: US 12,064,227 B2
(45) Date of Patent: Aug. 20, 2024

(54) AUTOMATIC DETERMINATION OF B-VALUES FROM DIFFUSION-WEIGHTED MAGNETIC RESONANCE IMAGES

(71) Applicant: International Business Machines Corporation, Armonk, NY (US)

(72) Inventors: Amin Katouzian, Lexington, MA (US); Marwan Sati, Mississauga (CA); Arkadiusz Sitek, Ashland, MA (US); Benedikt Graf, Charlestown, MA (US); Aly Mohamed, Acton, MA (US); Kourosh Jafari-Khouzani, Rego Park, NY (US); Frederic Commandeur, Paris (FR); Omid Bonakdar Sakhi, North York (CA)

(73) Assignee: International Business Machines Corporation, Armonk, NY (US)

( * ) Notice: Subject to any disclaimer, the term of this patent is extended or adjusted under 35 U.S.C. 154(b) by 372 days.

(21) Appl. No.: 17/681,324

(22) Filed: Feb. 25, 2022

(65) Prior Publication Data

US 2023/0270347 A1    Aug. 31, 2023

(51) Int. Cl.
*G06T 7/00* (2017.01)
*A61B 5/055* (2006.01)
(Continued)

(52) U.S. Cl.
CPC .......... *A61B 5/055* (2013.01); *G01R 33/5608* (2013.01); *G01R 33/56341* (2013.01);
(Continued)

(58) Field of Classification Search
CPC ................ A61B 5/055; A61B 2576/00; G01R 33/5608; G01R 33/56341; G06T 7/97;
(Continued)

(56) References Cited

U.S. PATENT DOCUMENTS 9,709,651 B2 * 7/2017 Wong ............... G01R 33/56341
2018/0356486 A1 * 12/2018 Yang .................... A61B 5/0037
(Continued)

FOREIGN PATENT DOCUMENTS

CN    106199473 A  * 12/2016  ......... G01R 33/5608
CN    106199473 A     12/2016
(Continued)

OTHER PUBLICATIONS

Birbiri, Ufuk C. et al., "Investigating the Performance of Generative Adversarial Networks for Prostate Tissue Detection and Segmentation", Journal of Imaging, 6, 83, 2020, Published: Aug. 24, 2020, doi:10.3390/jimaging6090083, 15 pages.
(Continued)

*Primary Examiner* — Ted W Barnes
(74) *Attorney, Agent, or Firm* — Stephen J. Walder, Jr.; Gavin Giraud

(57) ABSTRACT

A mechanism is provided in a data processing system for automatic determination of b-value difference from diffusion-weighted (DW) images. The mechanism receives a series of images wherein a first image has a first b-value and a second image has an unknown b-value. The mechanism applies a generative adversarial network (GAN) model to estimate a difference between b-values in the series of images. The mechanism determines a b-value for the second image based on the first b-value and the estimated difference between b-values.

20 Claims, 5 Drawing Sheets

(51) Int. Cl.
*G01R 33/56* (2006.01)
*G01R 33/563* (2006.01)
*G16H 30/40* (2018.01)

(52) U.S. Cl.
CPC ............... *G06T 7/97* (2017.01); *G16H 30/40* (2018.01); *A61B 2576/00* (2013.01); *G06T 2207/10092* (2013.01); *G06T 2207/20084* (2013.01); *G06T 2207/30004* (2013.01)

(58) Field of Classification Search
CPC . G06T 2207/10092; G06T 2207/20084; G06T 2207/30004; G16H 30/40
See application file for complete search history.

(56) References Cited

U.S. PATENT DOCUMENTS

| | | | |
|---|---|---|---|
| 2021/0124004 A1* | 4/2021 | Drobnitzky | G01R 33/56341 |
| 2021/0199743 A1* | 7/2021 | Yap | G01R 33/56341 |
| 2021/0239780 A1* | 8/2021 | Fan | G16H 30/40 |
| 2022/0179030 A1* | 6/2022 | Tian | A61B 5/055 |
| 2022/0187404 A1* | 6/2022 | Ermes | G01R 33/56341 |
| 2023/0186463 A1* | 6/2023 | Wei | G06N 3/0442 |
| | | | 382/128 |

FOREIGN PATENT DOCUMENTS

| | | | | | |
|---|---|---|---|---|---|
| CN | 107219483 A | * | 9/2017 | ....... | G01R 33/56341 |
| CN | 107240125 A | * | 10/2017 | ........... | G06T 11/003 |
| CN | 107240125 A | | 10/2017 | | |
| CN | 106199473 B | * | 4/2019 | ......... | G01R 33/5608 |
| CN | 111445546 A | | 7/2020 | | |
| CN | 112419203 A | * | 2/2021 | ........... | G06N 3/0454 |
| CN | 112419203 A | | 2/2021 | | |
| CN | 112785540 A | * | 5/2021 | ........... | G06K 9/6215 |
| CN | 112785540 A | | 5/2021 | | |
| CN | 111445546 B | * | 5/2023 | ........... | G06T 11/003 |
| DE | 102019216559 A1 | * | 4/2021 | ........... | G01R 33/385 |
| WO | WO2019/238804 A1 | | 12/2019 | | |
| WO | WO-2019238804 A1 | * | 12/2019 | ........... | G06F 18/214 |
| WO | WO-2020168641 A1 | * | 8/2020 | | |

OTHER PUBLICATIONS

Chiou, Eleni et al., "Synthesizing VERDICT maps from standard diffusion mp-MRI data using GANs", https://www.biorxiv.org/content/10.1101/2021.02.16.431521v1.full,posted Feb. 17, 2021, bioRxiv, 8 pages.

Fan, Ming et al., "Generative adversarial network-based super-resolution of diffusion-weighted imaging: Application to tumour radiomics in breast cancer", NMR in Biomedicine, vol. 33, iss. 8, Aug. 2020, e4345, First published: Jun. 10, 2020, https://doi.org/10.1002/nbm.4345, 12 pages.

Hu, Lei et al., "Synthesizing High-b-Value Diffusion-weighted Imaging of the Prostate Using Generative Adversarial Networks", Radiology: Artificial Intelligence (2021): e200237. Published online: Jun. 2, 2021, https://pubs.rsna.org/doi/abs/10.1148/ryai.2021200237, 2 pages.

Kamphenkel, Jennifer et al., "Domain Adaptation for Deviating Acquisition Protocols in CNN-based Lesion Classification on Diffusion-Weighted MR Images", arXiv:1807.06277v1 [cs.CV] Jul. 17, 2018, 8 pages.

Wang, Zhiwei et al., "Semi-supervised mp-MRI Data Synthesis with StitchLayer and Auxiliary Distance Maximization", arXiv:1812.06625v1 [cs.LG], Dec. 17, 2018, 10 pages.

International Search Report and Written Opinion dated May 10, 2023 for International Application No. PCT/CN2023/075386, 7 pages.

* cited by examiner

AUTOMATIC DETERMINATION OF B-VALUES FROM DIFFUSION-WEIGHTED MAGNETIC RESONANCE IMAGES

BACKGROUND

The present application relates generally to an improved data processing apparatus and method and more specifically to mechanisms for automatically determining b-values from diffusion-weighted magnetic resonance images.

Diffusion-weighted imaging (DWI) is the use of specific magnetic resonance imaging (MRI) sequences as well as software that generates images from the resulting data that uses the diffusion of water molecules to generate contrast in magnetic resonance images. DWI allows the mapping of the diffusion process of molecules, mainly water, in biological tissues, in vivo and non-invasively. Molecular diffusion in tissues is not random but reflects interactions with many obstacles, such as macromolecules, fibers, and membranes. Water molecule diffusion patterns can therefore reveal microscopic details about tissue architecture, either normal or in a diseased state.

In diffusion weighted imaging (DWI), the intensity of each image element (voxel) reflects the best estimate of the rate of water diffusion at that location. Because the mobility of water is driven by thermal agitation and highly dependent on its cellular environment, the hypothesis behind DWI is that findings may indicate pathologic change. For instance, DWI is more sensitive to early changes after a stroke than more traditional MRI measurements such as T1 or T2 relaxation rates.

Diffusion-weighted images are very useful to diagnose vascular strokes in the brain. It is also used more and more in the staging of non-small-cell lung cancer. DWI is most applicable when the tissue of interest is dominated by isotropic water movement, e.g., grey matter in the cerebral cortex and major brain nuclei, or in the body, where the diffusion rate appears to be the same when measured along any axis. However, DWI also remains sensitive to T1 and T2 relaxation. To entangle diffusion and relaxation effects on image contrast, one may obtain quantitative images of the diffusion coefficient, or more exactly the apparent diffusion coefficient (ADC). The ADC concept was introduced to take into account the fact that the diffusion process is complex in biological tissues and reflects several different mechanisms.

An apparent diffusion coefficient (ADC) image, or an ADC map, is an image that more specifically shows diffusion than conventional DWI, by eliminating the T2 weighting that is otherwise inherent to conventional DWI. ADC imaging does so by acquiring multiple conventional DWI images with different amounts of DWI weighting, and the change in signal is proportional to the rate of diffusion. A b-value reflects the strength and the gradient used for generating the DW images. In general, there is no optimal set of b-values to be taken and therefore the DW images are taken at multiple b-values. The ADC map is often generated using DW images taken at multiple b-values.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system for automatic determination of b-value difference from diffusion-weighted (DW) images. The method comprises receiving a series of images wherein a first image has a first b-value and a second image has an unknown b-value. The method further comprises applying a generative adversarial network (GAN) model to estimate a difference between b-values in the series of images. The method further comprises determining a b-value for the second image based on the first b-value and the estimated difference between b-values. The illustrative embodiment provides a computer-implemented technique for determining b-values for images for which the b-values are missing.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In one illustrative embodiment, a computer program product comprises a computer readable storage medium having a computer readable program stored therein. The computer readable program, when executed on a computing device, causes the computing device to receive a series of DW images wherein a first image has a first b-value and a second image has an unknown b-value, apply a generative adversarial network (GAN) model to estimate a difference between b-values in the series of DW images, and determine a b-value for the second image based on the first b-value and the estimated difference between b-values.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

In one illustrative embodiment, an apparatus comprises a processor and a memory coupled to the processor. The memory comprises instructions which, when executed by the processor, cause the processor to receive a series of DW images wherein a first image has a first b-value and a second image has an unknown b-value, apply a generative adversarial network (GAN) model to estimate a difference between b-values in the series of DW images, and determine a b-value for the second image based on the first b-value and the estimated difference between b-values.

In one example embodiment, applying the GAN model comprises constructing a latent space with a latent variable for learning to generate a synthetic apparent diffusion coefficient (ADC) map for identifying unknown b-values in the series of DW images and a loss function based on a relationship between the ADC map and the spatial relationship between images in the series of DW images. This embodiment provides information for applying the GAN model, thus achieving greater accuracy.

In another example embodiment, constructing the latent space comprises applying encoders to the images in the series of DW images. In another example embodiment, the latent space comprises a latent variable and a difference value representing a difference between b-values. In yet another example embodiment, the GAN model comprises a generator, a discriminator, and an estimator. These embodiments provide computer-implemented techniques for configuring the GAN model specifically for determining b-values, thus improving effectiveness and accuracy.

In another example embodiment, the GAN model has an identify-preserving loss ($L_{identity}$) function as follows:

$$L_{identity} = \left(2\alpha_Z \alpha_{S_{ADC_{\Delta b}}}\right)^{-1} \|Z - E(S_{ADC_{\Delta b}})\|_2^2$$

where the α values are parameters for normalization and are as follows:

$$\alpha_x = \sigma_x^{-1} \|x - \mu_x\|.$$

This embodiment specifically configures the GAN Model to determine b-values with greater accuracy.

In yet another example embodiment, the GAN model has a pixel loss ($L_{pixel}$) function as follows:

$$L_{pixel} = \frac{1}{\Delta b \times L \times W \times H} \|G(z, \Delta b) - |\ln(S_{b_2}/S_{b_1})|\|_2^2.$$

This embodiment specifically configures the GAN Model to determine b-values with greater accuracy.

In another example embodiment, the GAN model has a regression loss ($L_{regression}$) function as follows:

$$L_{regression} = \mathbb{E}_{z \sim p_z} \|R(G(z, \Delta b)) - \Delta b\|_2^2.$$

This embodiment specifically configures the GAN Model to determine b-values with greater accuracy.

In yet another example embodiment, the GAN model has discriminator and generator losses ($L_{GAN-D}$, $L_{GAN-G}$) as follows:

$$L_{GAN-D} = \mathbb{E}_{z, \Delta b \sim p_{(z, \Delta b)}}[-\log D(z, \Delta b)] + \mathbb{E}_{z, \Delta b \sim p_{(z, \Delta b)}}[-\log(1 - D(G(z, b)))]$$

$$L_{GAN-G} = \mathbb{E}_{z, \Delta b \sim p_{(z, \Delta b)}}[\log(1 - D(G(z, \Delta b)))].$$

This embodiment specifically configures the GAN Model to determine b-values with greater accuracy.

In another example embodiment, the GAN model has objective functions for the generator and the discriminator as follows:

$$L_G = \gamma_i L_{identity} + \gamma_p L_{pixel} + \gamma_r L_{regression} + \gamma_g L_{GAN-G}$$

$$L_D = L_{GAN-D},$$

wherein the objective is to minimize both objective functions $L_G$ and $L_D$. This embodiment specifically configures the GAN Model to determine b-values with greater accuracy.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
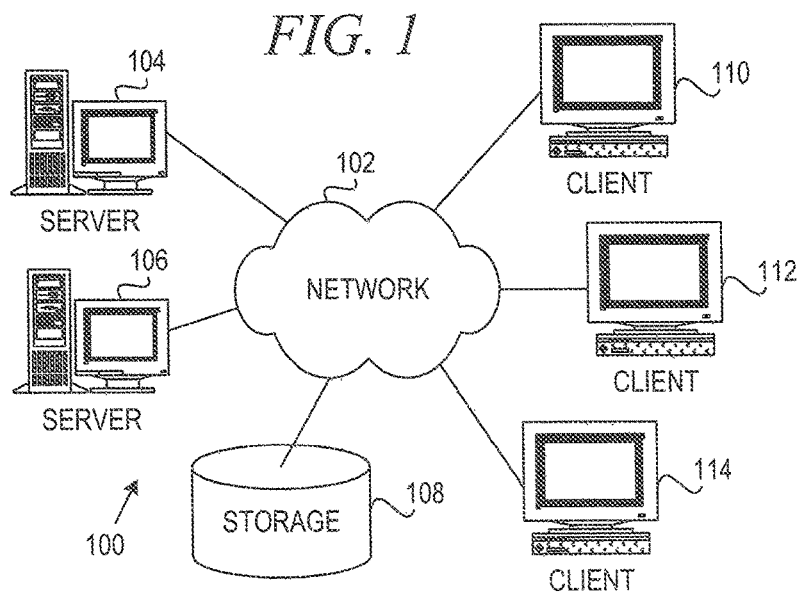
FIG. 1 is an example diagram of a distributed data processing system in which aspects of the illustrative embodiments may be implemented.

In magnetic resonance imaging, diffusion-weighted (DW) images are taken for measuring and visualizing the motions of water molecules within an organ. DW images provide valuable information about tissues. A b-value reflects the strength and the gradient used for generating a DW image. Digital Imaging and Communications in Medicine (DICOM) is the standard for the communication and management of medical imaging information and related data. DICOM is most commonly used for storing and transmitting medical images enabling the integration of medical imaging devices such as scanners, servers, workstations, printers, network hardware, and picture archiving and communication systems (PACS) from multiple manufacturers. It has been widely adopted by hospitals and is making inroads into smaller applications such as dentists' and doctors' offices. There is no mandatory (Type I) DICOM tag for storing b-values. The b-values sometime are stored in private DICOM tags that are often removed due to anonymization. The b-value could be captured from SeriesDescription tag or SequenceName tag, etc., which are not Type I tags and are subject to variations, which makes string matching challenging. In other cases, the b-value can be totally missing in DICOM tags. Without knowing the difference between b-values ($\Delta b = |b_2 - b_1|$), ADC maps cannot be generated accurately.

A similar problem can be associated with computerized tomography (CT) contrast imaging where acquisition time points are missing and cannot be retrieved from DICOM tags.

The illustrative embodiments provide a computer-implemented b-value determination engine for automatically determining b-value differences from diffusion-weighted images. Given a diffusion-weighted imaging series, the b-value determination engine determines a difference in b-values ($\Delta b$) between each pair of DW images in the series. Series are DW image series taken at $b_1, b_2, \ldots, b_n$. The b-value determination engine is configured as a generative adversarial network (GAN) for regression. A GAN is a class of machine learning frameworks in which two neutral networks contest with each other in a game (in the form of a zero-sum game, where one agent's gain is another agent's loss). Given a training set, this technique learns to generate new data with the same statistics as the training set. The core idea of a GAN is based on "indirect" training through a discriminator, which itself is also updated dynamically. This basically means that the generator is not trained to minimize the distance to a specific image, but rather to fool the discriminator. This enables the model to learn in an unsupervised manner.

At least two DWI images, taken at two b-values ($b_1$ and $b_2$), are required. The computer-implemented b-value determination engine uses encoders to construct a latent space for learning a transform from the original DWI series to an ADC map. To achieve this, the illustrative embodiment uses a latent variable (z). The illustrative embodiment incorporates the spatial relationship between ADC map and original DWI intensities into a loss function.

Thus, the illustrative embodiments use an image-based artificial intelligence (AI) model for automatic estimation of difference between two b-values from a pair of DW images. The illustrative embodiments allow accurate construction of ADC maps in case b-values are missing or not accessible. The illustrative embodiments use AI models to determine information that is not obtainable using manual or mental processes. The results of the illustrative embodiments enable better and more reliable lesion characterization in magnetic resonance imaging or computerized tomography.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software executing on computer hardware, specialized computer hardware and/or firmware, or any combination thereof that performs the specified functions including, but not limited to, any use of a general and/or specialized processor in combination with appropriate software loaded or stored in a machine readable memory and executed by the processor to thereby specifically configure the processor to perform the specific functions of the illustrative embodiments. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
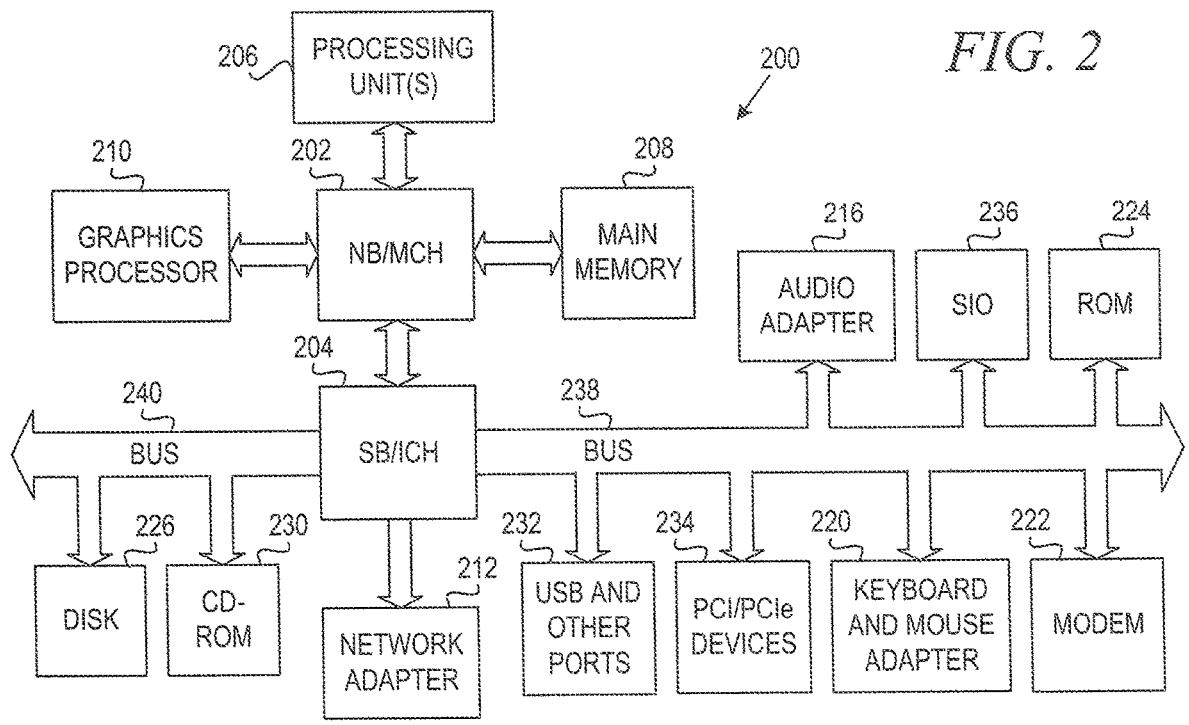
FIG. 2 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational, and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 104, may be specifically configured to implement a b-value determination engine for automatic determination of b-value differences from diffusion-weighted images. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general-purpose computing device. Moreover, as described hereafter, the implementation of the mechanisms of the illustrative embodiments improves the functionality of the computing device and provides a useful and concrete result that facilitates automatic determination of b-values and b-value differences.

As noted above, the mechanisms of the illustrative embodiments utilize specifically configured computing devices, or data processing systems, to perform the operations for determining b-values from diffusion-weighted images. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external effects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. In a client device, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System P® computer system, Power™ processor-based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to the b-value determination engine.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
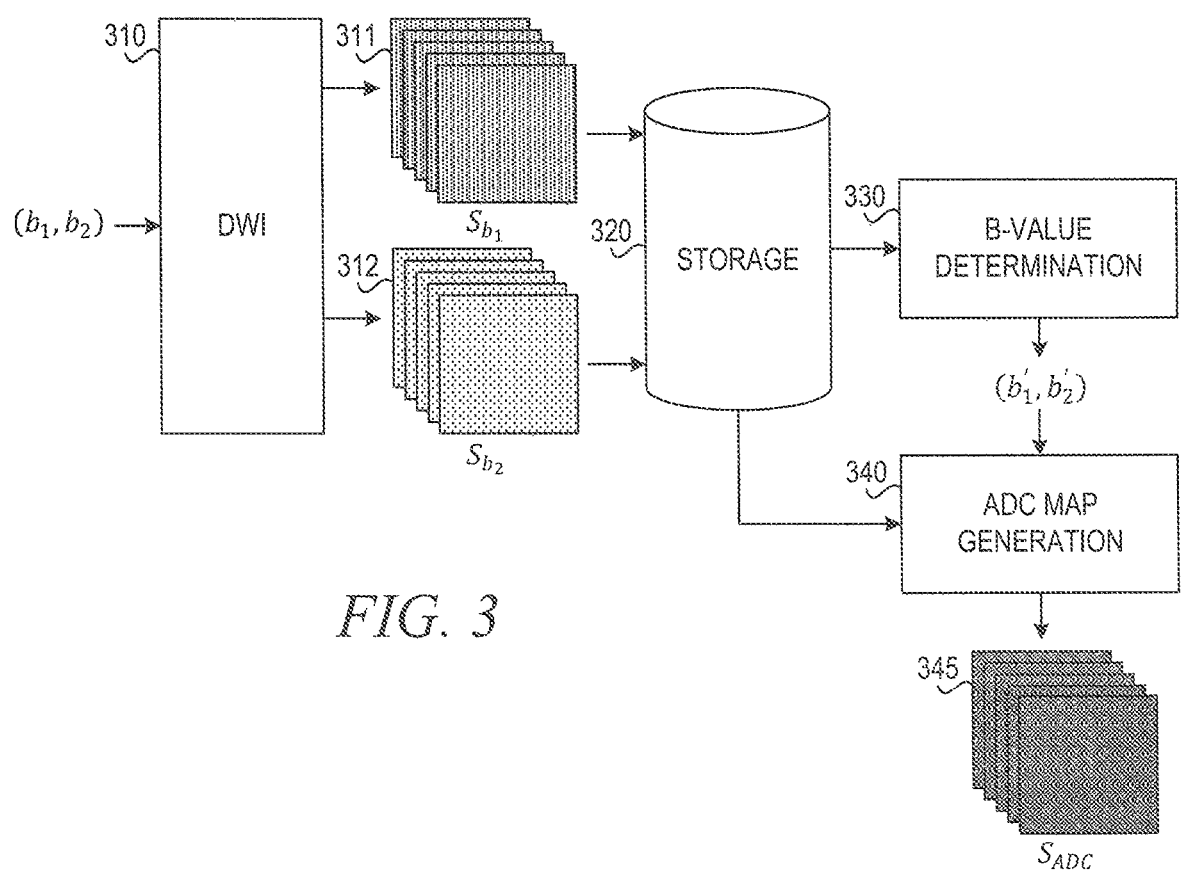
FIG. 3 is a block diagram illustrating a system for diffusion-weighted imaging with b-value detection in accordance with an illustrative embodiment.

FIG. 3 is a block diagram illustrating a system for diffusion-weighted imaging with b-value detection in accordance with an illustrative embodiment. A diffusion-weighted imaging (DWI) system 310 generates series of images, $S_{b_1}$ 311 and $S_{b_2}$ 312 based on a plurality of b-values ($b_1$, $b_2$). In one example embodiment, DWI system 310 is a diffusion-weighted magnetic resonance imaging (DW-MRI) system. The DWI system 310 stores the images in storage 320. As previously discussed, medical images may be stored according to the Digital Imaging and Communications in Medicine (DICOM) standard with Type I DICOM tags. However, there is no universal way to store b-values because there is no Type I tag for b-values. In some cases, b-values may be stored in private tags that may be removed during anonymization or for other reasons. In other cases, b-values may not be stored for one reason or another.

In the embodiment shown in FIG. 3, b-value determination engine 330 receives images 311, 312 from storage 320 and determines the b-values ($b'_1$, $b'_2$) of the images or a difference between b-values ($\Delta b$). For instance, image series $S_b$ 311 may be stored with its corresponding b-value ($b_1$), while image series $S_{b_2}$ 312 may be missing tag for its corresponding b-value in storage 320. The b-value determination engine 330 uses a generative adversarial network (GAN) model to learn how to transform two or more image series into an apparent diffusion coefficient (ADC) map and to use the ADC map to estimate a difference in b-values ($\Delta b$). With one known b-value, the other b-value can easily be estimated based on the estimated $\Delta b$. ADC map generation engine 340 then uses the determined b-values to generate ADC map $S_{ADC}$ 345.

Figure 4A:
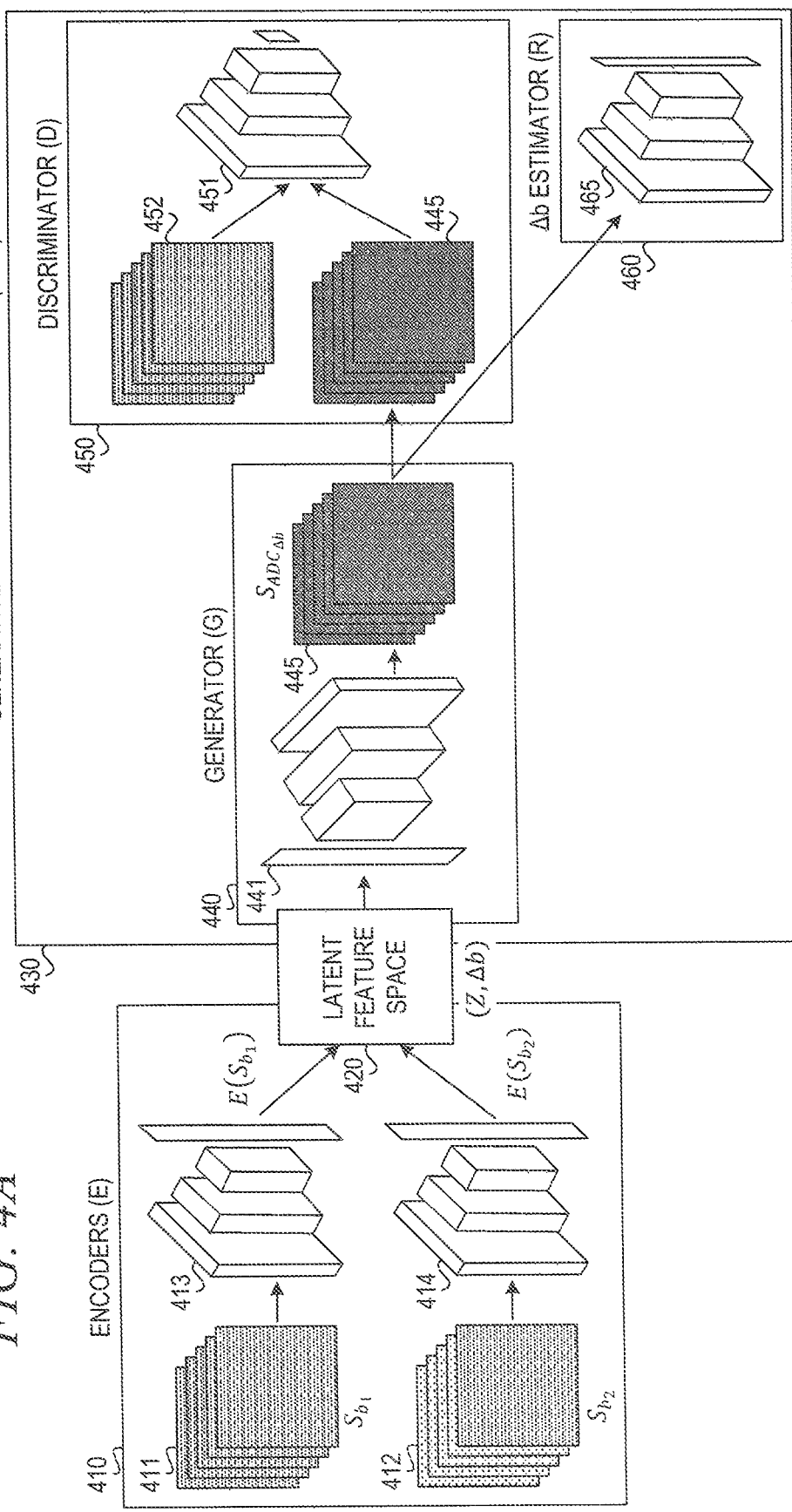
FIGS. 4A-4C illustrate a generative adversarial network model for automatically determining b-values from diffusion-weighted images in accordance with an illustrative embodiment.
Figure 4B:
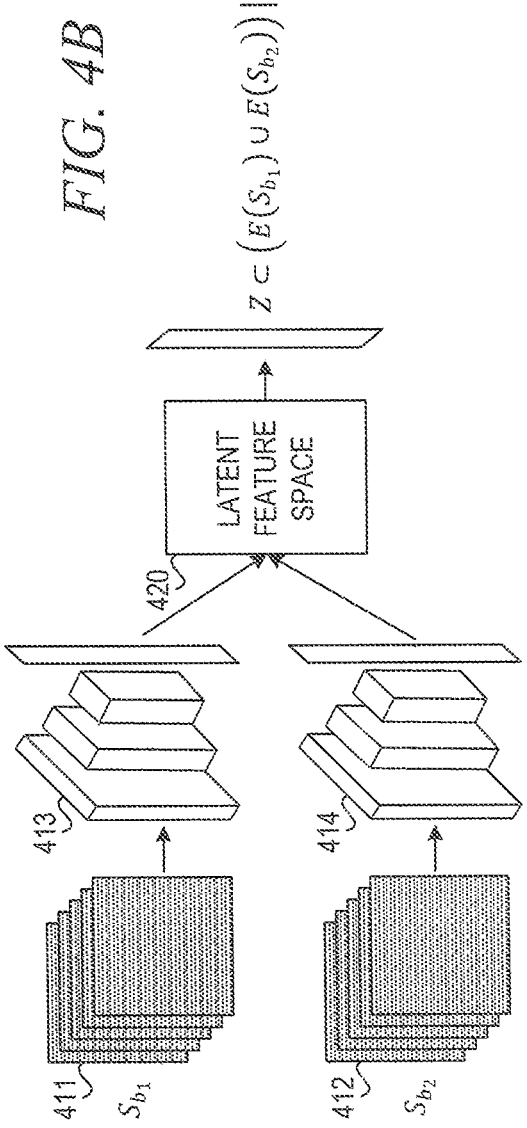
Figure 4C:
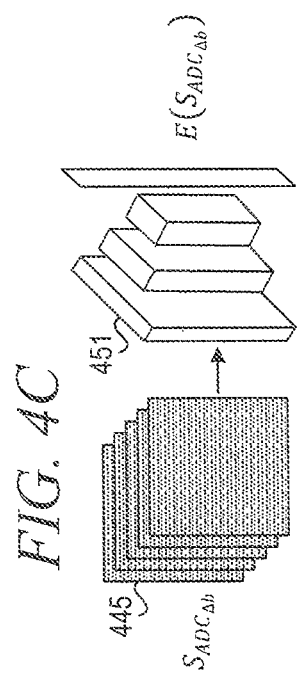

FIGS. 4A-4C illustrate a generative adversarial network model for automatically determining b-values from diffusion-weighted images in accordance with an illustrative embodiment. With reference to FIG. 4A, encoders (E) 410 encode image series into latent feature space (z, $\Delta b$) 420. In the depicted example, encoder 413 receives image series $S_{b_1}$ 411 and generates encoding $E(S_{b_1})$, and encoder 414 receives image series $S_{b_2}$ 412 and generates encoding $E(S_{b_2})$.

In one example embodiment, encoders 413, 414 are convolutional encoders. Encoders 413, 414 construct a latent space 420 for learning a transform from the original DWI series 411, 412 to ADC map 445. To achieve this, the illustrative embodiment introduces latent variable (z).

Generative adversarial network (GAN) 430 includes generator (G) 440, discriminator (D) 450, and $\Delta b$ estimator (R) 460. Generator 440 receives latent space (z, $\Delta b$) 420 and generates ADC map $S_{ADC_{\Delta b}}$ 445. In the depicted example, generator 440 uses a deconvolutional generator 441. The convolutional encoders 413, 414 and the deconvolutional generator uses discriminative network 451 to learn the ADC map transformation in latent features space 420.

In the depicted example, discriminative network 451 receives the generated ADC map $S_{ADC_{\Delta b}}$ 445 and true ADC map 452 to test the generator 440. The generative network 441 generates candidates while the discriminative network 451 evaluates them. The contest operates in terms of data distributions. Typically, the generative network 441 learns to map from latent space 420 to a data distribution of interest, while the discriminative network 451 distinguishes candidates produced by the generator 441 from the true data distribution. The objective of training generative network 441 is to increase the error rate of the discriminative network (i.e., "fool" the discriminator network 451 by producing novel candidates that the discriminator thinks are not synthesized (are part of the true data distribution)).

A known dataset serves as the initial training data for the discriminator 450. Training discriminator 450 involves presenting it with samples from the training dataset until it achieves acceptable accuracy. The generator network 441 trains based on whether it succeeds in fooling the discriminator. In the depicted example, the generator network 441 is seeded with a randomized input that is sampled from latent space 420. Thereafter, candidates synthesized by the generator network 441 are evaluated by the discriminator network 451 against ADC series 452 generated by the MRI machine. Discriminator network 451 determines how close the estimated ADC map 445 is to the original ADC map 452. Independent backpropagation procedures are applied to both networks so that the generator produces better samples, while the discriminator becomes more skilled at flagging synthetic samples.

The $\Delta b$ estimator (R) 460 uses a convolutional encoder 465 to estimate the $\Delta b$ value using the ADC map $S_{ADC_{\Delta b}}$ 445 as input. The $\Delta b$ value can then be used to determine a missing b-value.

Turning to FIG. 4B, the latent feature space 420 is defined as follows:

$$Z \subset (E(S_{b_1}) \cup E(S_{b_2})) | S_{b_1} \to E(S_{b_1}); S_{b_2} \to E(S_{b_2})$$

With reference now to FIG. 4C, encoder 451 receives the generated ADC map $S_{ADC_{\Delta b}}$ 445 as input and generates $E(S_{ADC_{\Delta b}})$.

Training of the GAN 430 depends on the following losses:
1. Identity-preserving loss ($L_{identity}$);
2. Pixel loss ($L_{pixel}$);
3. Regression loss ($L_{regression}$);
4. GAN losses ($L_{GAN-D}$, $L_{GAN-G}$).

The identity-preserving loss ($L_i$) is as follows:

$$L_{identity} = \left(2\alpha_Z \alpha_{S_{ADC_{\Delta b}}}\right)^{-1} \left\| Z - E\left(S_{ADC_{\Delta b}}\right) \right\|_2^2$$

where the α values are parameters for normalization and are as follows:

$$\alpha_x = \sigma_x^{-1} \|x - \mu_x\|,$$

where the data x is normalized subtracting the mean μ and dividing by the standard deviation σ.

The pixel loss ($L_{pixel}$) is as follows:

$$L_{pixel} = \frac{1}{\Delta b \times L \times W \times H} \|S_{ADC_{\Delta b}} - |\ln(S_{b_2}/S_{b_1})|\|_2^2$$

$$= \frac{1}{\Delta b \times L \times W \times H} \|G(z, \Delta b) - |\ln(S_{b_2}/S_{b_1})|\|_2^2$$

The regression loss ($L_{regression}$) is as follows:

$$L_{regression} = \mathbb{E}_{z \sim p_z} \|R(G(z, \Delta b)) - \Delta b\|_2^2$$

The GAN losses ($L_{GAN-D}$, $L_{GAN-G}$) are as follows:

$$L_{GAN-D} = \mathbb{E}_{z, \Delta b \sim p_{(z, \Delta b)}}[-\log D(z, \Delta b)] + \mathbb{E}_{z, \Delta b \sim p_{(z, \Delta b)}}[-\log(1 - D(G(z, \Delta b)))]$$

$$L_{GAN-G} = \mathbb{E}_{z, \Delta b \sim p_{(z, \Delta b)}}[\log(1 - D(G(z, \Delta b)))],$$

where p represents a probability distribution function.

The objective functions for G and D are as follows:

$$L_G = \gamma_i L_{identity} + \gamma_p L_{pixel} + \gamma_r L_{regression} + \gamma_g L_{GAN-G}$$

$$L_D = L_{GAN-D}$$

The goal is to minimize both objective functions $L_G$ and $L_D$.

Figure 5:
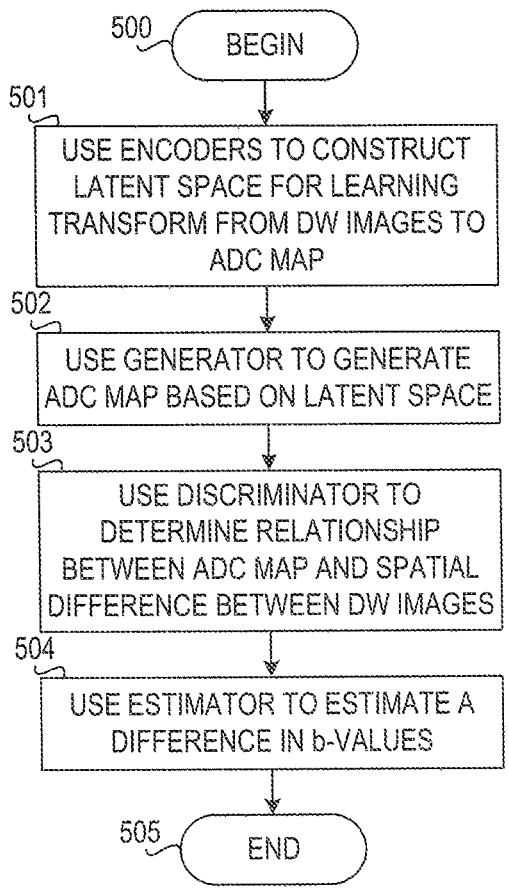
FIG. 5 is a flowchart illustrating operation of a generative adversarial network model for automatically determining b-values from diffusion-weighted images in accordance with an illustrative embodiment.

FIG. 5 is a flowchart illustrating operation of a generative adversarial network model for automatically determining b-values from diffusion-weighted images in accordance with an illustrative embodiment. Operation begins (block 500), and the generative adversarial network (GAN) model uses encoders to construct latent space for learning transform from DW images to an ADC map (block 501). The GAN model uses a generator to generate ADC maps from the latent space (block 502). The GAN model then uses a discriminator to determine a relationship between the ADC map and a special difference between DW images (block 503). Thereafter, the GAN model uses an estimator to estimate a difference in b-values (block 504), and operation ends (block 505).

Figure 6:
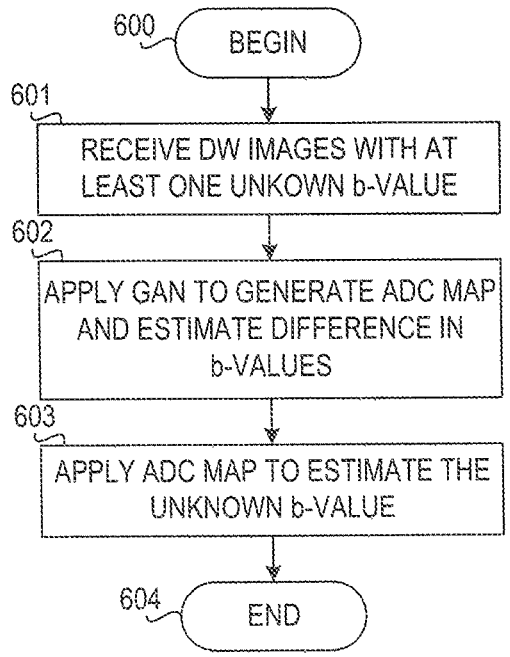
FIG. 6 is a flowchart illustrating operation of a system for diffusion-weighted imaging with b-value detection in accordance with an illustrative embodiment.

FIG. 6 is a flowchart illustrating operation of a system for diffusion-weighted imaging with b-value detection in accordance with an illustrative embodiment. Operation begins (block 600), and the system receives DW images with at least one unknown b-value (block 601). The system applies the GAN to generate an ADC map and to estimate a difference in b-values between the DW images (block 602). Thereafter, the system applies the ADC map to estimate the unknown b-value (block 603), and operation ends (block 604).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication-based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, for automatic determination of b-value difference from diffusion-weighted (DW) images, the method comprising:

receiving a series of DW images wherein a first image has a first b-value and a second image has an unknown b-value;

applying a generative adversarial network (GAN) model to estimate a difference between b-values in the series of DW images; and determining a b-value for the second image based on the first b-value and the estimated difference between b-values.

2. The method of claim 1, wherein applying the GAN model comprises constructing a latent space with a latent variable for learning to generate a synthetic apparent diffusion coefficient (ADC) map for identifying unknown b-values in the series of DW images and a loss function based on a relationship between the ADC map and the spatial relationship between images in the series of DW images.

3. The method of claim 2, wherein constructing the latent space comprises applying encoders to the images in the series of DW images.

4. The method of claim 2, wherein the latent space comprises a latent variable and a difference value representing a difference between b-values.

5. The method of claim 1, wherein the GAN model comprises a generator, a discriminator, and an estimator.

6. The method of claim 5, wherein GAN model has an identify-preserving loss ($L_{identity}$) function as follows:

$$L_{identity} = \left(2\alpha_Z \alpha_{S_{ADC_{\Delta b}}}\right)^{-1} \|Z - E(S_{ADC_{\Delta b}})\|_2^2$$

where the $\alpha$ values are parameters for normalization and are as follows:

$$\alpha_x = \sigma_x^{-1} \|x - \mu_x\|.$$

7. The method of claim 5, wherein the GAN model has a pixel loss ($L_{pixel}$) function as follows:

$$L_{pixel} = \frac{1}{\Delta b \times L \times W \times H} \|G(z, \Delta b) - |\ln(S_{b_2}/S_{b_1})|\|_2^2.$$

8. The method of claim 5, wherein the GAN model has a regression loss ($L_{regression}$) function as follows:

$$L_{regression} = \mathbb{E}_{z \sim p_z} \|R(G(z,\Delta b)) - \Delta b\|_2^2.$$

9. The method of claim 5, wherein the GAN model has discriminator and generator losses ($L_{GAN-D}$, $L_{GAN-G}$) as follows:

$$L_{GAN-D} = \mathbb{E}_{z,\Delta b \sim p_{(z,\Delta b)}}[\log D(z,\Delta b)] + \mathbb{E}_{z,\Delta b \sim p_{(z,\Delta b)}}[-\log(1-D(G(z,b)))]$$

$$L_{GAN-G} = \mathbb{E}_{z,\Delta b \sim p_{(z,\Delta b)}}[\log(1-D(G(z,\Delta b)))].$$

10. The method of claim 5, wherein the GAN model has objective functions for the generator and the discriminator as follows:

$$L_G = \gamma_i L_{identity} + \gamma_p L_{pixel} + \gamma_r L_{regression} + \gamma_g L_{GAN-G}$$

$$L_D = L_{GAN-D},$$

wherein the objective is to minimize both objective functions $L_G$ and $L_D$.

11. A computer program product comprising a computer readable storage medium having a computer readable program stored therein, wherein the computer readable program, when executed on a computing device, causes the computing device to:
receive a series of DW images wherein a first image has a first b-value and a second image has an unknown b-value;
apply a generative adversarial network (GAN) model to estimate a difference between b-values in the series of DW images; and
determine a b-value for the second image based on the first b-value and the estimated difference between b-values.

12. The computer program product of claim 11, wherein applying the GAN model comprises constructing a latent space with a latent variable for learning to generate a synthetic apparent diffusion coefficient (ADC) map for identifying unknown b-values in the series of DW images and a loss function based on a relationship between the ADC map and the spatial relationship between images in the series of DW images.

13. The computer program product of claim 12, wherein constructing the latent space comprises applying encoders to the images in the series of DW images and wherein the latent space comprises a latent variable and a difference value representing a difference between b-values.

14. The computer program product of claim 11, wherein the GAN model comprises a generator, a discriminator, and an estimator.

15. The computer program product of claim 14, wherein GAN model has an identify-preserving loss ($L_{identity}$) function as follows:

$$L_{identity} = \left(2\alpha_Z \alpha_{S_{ADC_{\Delta b}}}\right)^{-1} \|Z - E(S_{ADC_{\Delta b}})\|_2^2$$

where the $\alpha$ values are parameters for normalization and are as follows:

$$\alpha_x = \sigma_x^{-1} \|x - \mu_x\|.$$

16. The computer program product of claim 14, wherein the GAN model has a pixel loss ($L_{pixel}$) function as follows:

$$L_{pixel} = \frac{1}{\Delta b \times L \times W \times H} \|G(z, \Delta b) - |\ln(S_{b_2}/S_{b_1})|\|_2^2.$$

17. The computer program product of claim 14, wherein the GAN model has a regression loss ($L_{regression}$) function as follows:

$$L_{regression} = \mathbb{E}_{z \sim p_z} \|R(G(z,\Delta b)) - \Delta b\|_2^2.$$

18. The computer program product of claim 14, wherein the GAN model has discriminator and generator losses ($L_{GAN-D}$, $L_{GAN-G}$) as follows:

$$L_{GAN-D} = \mathbb{E}_{z,\Delta b \sim p_{(z,\Delta b)}}[-\log D(z,\Delta b)] + \mathbb{E}_{z,\Delta b \sim p_{(z,\Delta b)}}[-\log(1-D(G(z,b)))]$$

$$L_{GAN-G} = \mathbb{E}_{z,\Delta b \sim p_{(z,\Delta b)}}[\log(1-D(G(z,\Delta b)))].$$

19. The computer program product of claim 14, wherein the GAN model has objective functions for the generator and the discriminator as follows:

$$L_G = \gamma_i L_{identity} + \gamma_p L_{pixel} + \gamma_r L_{regression} + \gamma_g L_{GAN-G}$$

$$L_D = L_{GAN-D},$$

wherein the objective is to minimize both objective functions $L_G$ and $L_D$.

20. An apparatus comprising:
a processor; and
a memory coupled to the processor, wherein the memory comprises instructions which, when executed by the processor, cause the processor to:
receive a series of DW images wherein a first image has a first b-value and a second image has an unknown b-value;
apply a generative adversarial network (GAN) model to estimate a difference between b-values in the series of DW images; and
determine a b-value for the second image based on the first b-value and the estimated difference between b-values.

* * * * *